United States Patent
Grass et al.

(10) Patent No.: US 8,184,883 B2
(45) Date of Patent: May 22, 2012

(54) MOTION COMPENSATED CT RECONSTRUCTION OF HIGH CONTRAST OBJECTS

(75) Inventors: Michael Grass, Buchholz in der Nordheide (DE); Dirk Schaefer, Hamburg (DE); Udo Van Stevendaal, Ahrensburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 698 days.

(21) Appl. No.: 12/093,458

(22) PCT Filed: Nov. 14, 2006

(86) PCT No.: PCT/IB2006/054232
§ 371 (c)(1),
(2), (4) Date: Dec. 4, 2008

(87) PCT Pub. No.: WO2007/060572
PCT Pub. Date: May 31, 2007

(65) Prior Publication Data
US 2009/0141935 A1 Jun. 4, 2009

(30) Foreign Application Priority Data
Nov. 24, 2005 (EP) .................................. 05111216

(51) Int. Cl.
*G06K 9/00* (2006.01)
*A61B 6/03* (2006.01)
(52) U.S. Cl. ............................. 382/131; 378/107; 378/21
(58) Field of Classification Search .................. 382/103, 382/131, 107, 130
See application file for complete search history.

(56) References Cited

U.S. PATENT DOCUMENTS

| | | | |
|---|---|---|---|
| 7,418,073 B2 * | 8/2008 | Schlomka et al. | 378/6 |
| 7,426,256 B2 * | 9/2008 | Rasche et al. | 378/8 |
| 7,545,903 B2 * | 6/2009 | Kohler et al. | 378/8 |
| 7,672,490 B2 * | 3/2010 | Kohler et al. | 382/128 |
| 2002/0015468 A1 * | 2/2002 | Kohler et al. | 378/4 |
| 2004/0081270 A1 | 4/2004 | Heuscher | |
| 2004/0136490 A1 * | 7/2004 | Edic et al. | 378/4 |
| 2007/0183639 A1 * | 8/2007 | Kohler et al. | 382/131 |
| 2008/0056547 A1 * | 3/2008 | Kokubun et al. | 382/128 |
| 2009/0074133 A1 * | 3/2009 | Nielsen et al. | 378/19 |

FOREIGN PATENT DOCUMENTS

WO 2005008597 A2 1/2005

OTHER PUBLICATIONS

Crawford, C. R., et al.; Respiratory Compensation in Projection Imaging Using a Magnification and Displacement Model; 1996; IEEE Trans. on Medical Imaging; 15(3)327-332.
Feng, B., et al.; Estimation of the Rigid-Body Motion from Three-Dimensional Images Using a Generalized Center-of-Mass Points Approach; 2005; IEEE Nuclear Science Symposium Conf. Record; pp. 2173-2178.

(Continued)

*Primary Examiner* — William C Dowliing

(57) ABSTRACT

Cardiac CT imaging using gated reconstruction is currently limited in its temporal and spatial resolution. According to an exemplary embodiment of the present invention, an examination apparatus is provided in which an identification of a high contrast object is performed. This high contrast object is then followed through the phases, resulting in a motion vector field of the high contrast object, on the basis of which a motion compensated reconstruction is then performed.

18 Claims, 3 Drawing Sheets

OTHER PUBLICATIONS

Klein, G. J., et al.; Non-Rigid Summing of Gated PET via Optical Flow; 1997; IEEE Trans. on Nuclear Science; 44(4) 1509-1512.

Movassaghi, B., et al.; Automatic gating window positioning for 3D rotational coronary angiography (3DRCA); 2004; Proc. SPIE-Medical Imaging; vol. 5370:1932-1942.

Movassaghi, B., et al.; 3D coronary reconstruction from calibrated motion-compensated 2D projections; 2003; International Congress Series; 1256:1079-1084.

Ross, J. C., et al.; Registration and Integration for Fluoroscopy Device Enhancement; 2005; Medical Image Computing and Computer-Assisted Intervention-MICCAI-Lecture notes in Computer Science; vol. 3749:851-858.

Hemmendorff M.: "Motion Estimation and Compensation in Medical Imaging"; Linkoping Studies in Science and Technology, Dissertation Thesis No. 703, Institute of Technology, Linkoping University, Jul. 2001, 84 page Document.

Zhou et al: "Calculation of 3D Internal Displacement Fields From 3D X-Ray Computer Tomographic Images"; Proc. R. Soc. Lond. A (1995), vol. 449, pp. 537-554.

Close et al: "Layer Decomposition of Coronary Angiograms"; Medical Imaging 2000: Image Processing, Proceedings of SPIE, vol. 3979 (2000), pp. 1230-1234.

Kriminski et al: "Respiratory Correlated Cone-Beam Computed Tomography on an Isocentric C-Arm"; Institute of Physics Publishing, Phys. Med. Biol. Vol. 50, (2005), pp. 5263-5280.

Woodhouse et al: "Coronary Arteries: Restrospective Cardiac Gating Technique to Reduce Cardiac Motion Artifact At Spiral CT1"; Radiology, Aug. 1997, pp. 566-569.

Grangeat, P.: "Dynamic X-Ray Computed Tomography"; Dynct, IST-1999-10515, Departement Systemes Pour L'Information Et La Sante, Service Systemes Pour La Biologie Et La Sante, Grenoble, France, Annual Review 2002, 19 page Document.

* cited by examiner

MOTION COMPENSATED CT RECONSTRUCTION OF HIGH CONTRAST OBJECTS

The invention relates to the field of tomographic imaging. In particular, the invention relates to an examination apparatus for examination of an object of interest, to an image processing device, to a method of examination of an object of interest, a computer-readable medium and a program element.

Computed tomography (CT) is a process of using digital processing to generate a three-dimensional image of the internal of an object under investigation (object of interest) from a series of two-dimensional X-ray images taken around a single axis of rotation. The reconstruction of CT images can be done by applying appropriate algorithms.

One important application in the frame of the computer tomography is the so-called cardiac computer tomography, which is related to the reconstruction of a three-dimensional image of a beating heart.

Cardiac CT imaging using gated reconstruction is currently limited in its temporal and spatial resolution due to mechanical movement of the gantry and the fact that a finite angular span of projections has to be acquired for the reconstruction of each voxel.

It may be desirable to provide for an improved motion compensated reconstruction of an object of interest, in particular for an improved motion compensated CT reconstruction of high contrast objects.

According to an exemplary embodiment of the present invention, an examination apparatus for examination of an object of interest may be provided, the examination apparatus comprising a reconstruction unit adapted for reconstructing, on the basis of a data set, a first volume of the object of interest corresponding to a first phase point and a second volume of the object of interest corresponding to a second phase point. Furthermore, the examination apparatus may comprise a determination unit adapted for locating a high contrast object within the first volume and locating the high contrast object within the second volume, and for determining a motion vector field for the high contrast object, resulting in a motion vector connecting the position of the object in the first volume to the position of the object in the second volume, wherein the reconstruction unit is further adapted for performing a motion compensated reconstruction on the basis of the motion vector field.

Therefore, the examination apparatus may be adapted for performing a motion compensated reconstruction which can be used to improve the resolution of the reconstructed image in order to increase the signal-to-noise ratio or to suppress motion blurring. The reconstruction may comprise an identification of a high contrast object, which is then followed through the phases, resulting in a motion vector field of the high contrast object. A motion compensated reconstruction is then performed on the basis of the motion vector field.

Such a high contrast object may be, for example, a stent or a calcified plaque in case the region of interest is an internal organ, such as the heart, or a blood vessel.

According to another exemplary embodiment of the present invention, an image processing device for examination of an object of interest is provided, the image processing device comprising a memory for storing a data set of the object of interest, a reconstruction unit adapted for reconstructing, on the basis of the data set, a first volume of the object of interest corresponding to a first phase point and a second volume of the object of interest corresponding to a second phase point, and a determination unit adapted for locating a high contrast object within the first volume and locating the high contrast object within the second volume, and for determining a motion vector field for the high contrast object, resulting in a motion vector connecting the position of the object in the first volume to the position of the object in the second, wherein the reconstruction is further adapted for performing a motion compensated reconstruction on the basis of the motion vector field.

According to another exemplary embodiment of the present invention, a method of examination of an object of interest may be provided, the method comprising the steps of reconstructing, on the basis of a data set, a first volume of the object of interest corresponding to a first phase point and a second volume of the object of interest corresponding to a second phase point, locating a high contrast object within the first volume and locating the high contrast object within the second volume, and determining a motion vector field for the high contrast object, resulting in a resulting in a motion vector connecting the position of the object in the first volume to the position of the object in the second volume, wherein the reconstruction unit is further adapted for performing a motion compensated reconstruction on the basis of the motion vector field.

Beyond this, according to another exemplary embodiment of the present invention, a computer-readable medium is provided, in which a computer program of examination of an object of interest is stored which, when being executed by a processor, is adapted to carry out the above-mentioned method steps.

Furthermore, according to another exemplary embodiment of the invention, a program element of examination of an object of interest is provided, which, when being executed by a processor, is adapted to carry out the above-mentioned method steps.

The examination of the object of interest, i.e. the analysis of multi-cycle cardiac computer tomography data according to the invention, may be realized by the computer program, i.e. by software, or by using one or more special electronic optimization circuits, i.e. in hardware, or in hybrid form, i.e. by means of software components and hardware components.

In the following, further exemplary embodiments of the invention will be described. However, these embodiments apply also for the method of examination of an object of interest, for the computer-readable medium, for the image processing device and for the program element.

According to an exemplary embodiment of the present invention, the data set comprises projection data comprising of projections of the object of interest and electrocardiogram data of the object of interest.

According to another exemplary embodiment of the present invention, the data set is a cardiac CT data set, which may be acquired by rotating a radiation source, i.e. an X-ray source, and a detector unit around a heart of a human being. Based on this measurement, a plurality of projection data are obtained. Simultaneously, an electrocardiogram may be measured, wherein the data according to the electrocardiogram may later be used to select data which are appropriate for a subsequent reconstruction of the image of the heart, taking into account the beating cycles of the heart. After the measurement that is retrospectively, appropriate data may be selected using the electrocardiogram signals, wherein the selected data are then used for a further examination.

According to another exemplary embodiment of the present invention, the motion compensated reconstruction is performed for first projections of the projection data, wherein the first projections cover phases for which a motion compensation has been performed.

According to another exemplary embodiment of the present invention, the first projections, which cover phases for which a motion estimation and a motion compensation has been performed, are all projections of the data set, wherein the motion estimation covers a complete cardiac cycle.

Furthermore, according to another exemplary embodiment of the present invention, the first projections, which cover phases for which the motion estimation and the motion compensation have been performed, are a selection of the projections of the data set, wherein the motion estimation covers a complete cardiac cycle.

Furthermore, according to another exemplary embodiment of the present invention, the motion compensated reconstruction covers a sub-volume of at least one of the first volume and the second volume, wherein the sub-volume comprises the high contrast object, and wherein the motion vectors are used directly in the motion compensated reconstruction by modifying a voxel position in the sub-volume according to a cardiac phase of the projection to be back-projected.

Alternatively, according to another exemplary embodiment of the present invention, the motion compensated reconstruction covers at least one of the complete first volume and the complete second volume, wherein the motion compensated reconstruction is performed after at least one of a spatial extrapolation and a spatial interpolation of the motion vectors.

According to another exemplary embodiment of the present invention, the interpolation is a simple linear interpolation or a thin plate spline interpolation.

Furthermore, according to another exemplary embodiment of the present invention, the motion compensated reconstruction is performed after a temporal interpolation of the first and second motion vectors. For example, a first volume has been reconstructed at the phase point t0 and is to be reconstructed in a motion compensated manner. The reconstruction of this volume may require data acquired during the interval [t−Δt; t+Δt]. Furthermore, a second volume has been reconstructed at the phase point t−Δt and a third volume has been reconstructed at the phase point t+Δt, wherein the reconstruction of the second volume requires data acquired during the interval [t−2 Δt; t0] and wherein the reconstruction of the third volume requires data acquired during the interval [t0; t+2 Δt]. In this case, the calculated motion vector field may be temporally interpolated between t−Δt and t0. The order of the interpolation may correspond to the number of phase points (at which phase volumes have been measured).

Furthermore, according to another exemplary embodiment of the present invention, locating the high contrast object within the first volume and within the second volume comprises a location of a first high contrast object within the first volume, a location of a second high contrast object within the second volume, and a determination of a correspondence of the first high contrast object and the second high contrast object.

According to another exemplary embodiment of the present invention, the examination apparatus may be applied as a material testing apparatus, medical application apparatus, or a Micro CT apparatus adapted for performing a motion compensated reconstruction of high contrast objects. A field of application of the invention may be medical imaging, in particular cardiac CT, breathing gated CT or CT fluoroscopy.

According to another exemplary embodiment of the present invention, the examination apparatus may be applied as a computer tomography apparatus, a coherent scatter computed tomography apparatus, a positron emission tomography apparatus, a single photon emission computed tomography apparatus, and an interventional 3D rotational X-ray imaging system.

It should be noted in this context, that the present invention is not limited to computer tomography, but may always then be applied when motion compensation during reconstruction of a multi-dimensional data set has to be performed.

According to another exemplary embodiment of the present invention, the examination apparatus may further comprise a collimator arranged between the electromagnetic radiation source and the detector unit, wherein the collimator is adapted for collimating an electromagnetic radiation beam emitted by the electromagnetic radiation source to form a cone-beam or a fan-beam.

Furthermore, according to another exemplary embodiment of the present invention, the radiation source may be adapted for emitting a polychromatic radiation beam.

The program element according to another exemplary embodiment of the present invention may preferably be loaded into working memories of a data processor. The data processor may thus be equipped to carry out exemplary embodiments of the methods of the present invention. The computer program may be written in any suitable programming language, such as, for example, C++ and may be stored on a computer-readable medium, such as a CD-ROM. Also, the computer program may be available from a network, such as the WorldWideWeb, from which it may be downloaded into image processing units or processors, or any suitable computers.

It may be seen as the gist of an exemplary embodiment of the present invention that a motion compensated reconstruction is provided for cardiac CT, comprising an identification of a high contrast object which is followed through the phases, resulting in a motion vector field of the high contrast object. The motion compensated reconstruction is then performed on the basis of the motion vector field. This may improve the resolution of the reconstructed image, increase the signal-to-noise ratio or suppress motion blurring. The motion compensated reconstruction may be applied for high contrast objects moving with the heart such as calcified plaques or devices like stents.

These and other aspects of the present invention will become apparent from and elucidated with reference to the embodiments described hereinafter.

Exemplary embodiments of the present invention will be described in the following, with reference to the following drawings.

The illustration in the drawings is schematically. In different drawings, similar or identical elements are provided with the same reference numerals.

FIG. 1 shows an exemplary embodiment of a computed tomography scanner system according to the present invention.

Figure 1:
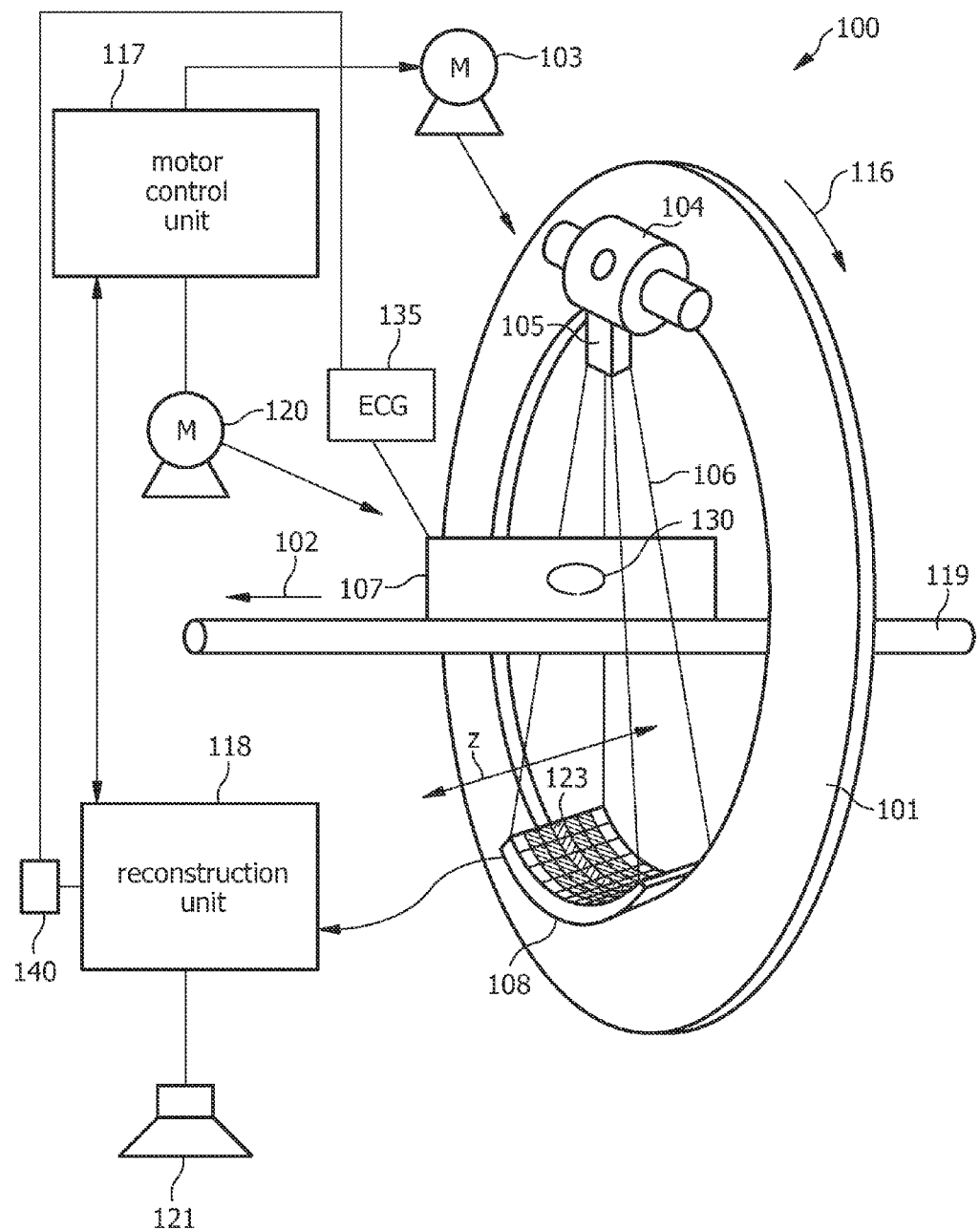
FIG. 1 shows a simplified schematic representation of an examination apparatus according to an exemplary embodiment of the present invention.

The computer tomography apparatus 100 depicted in FIG. 1 is a cone-beam CT scanner. However, the invention may also be carried out with a fan-beam geometry. The CT scanner depicted in FIG. 1 comprises a gantry 101, which is rotatable around a rotational axis 102. The gantry 101 is driven by means of a motor 103. Reference numeral 104 designates a source of radiation such as an X-ray source, which, according to an aspect of the present invention, emits polychromatic or monochromatic radiation.

Reference numeral 105 designates an aperture system which forms the radiation beam emitted from the radiation source to a cone-shaped radiation beam 106. The cone-beam 106 is directed such that it penetrates an object of interest 107 arranged in the center of the gantry 101, i.e. in an examination region of the CT scanner, and impinges onto the detector 108. As may be taken from FIG. 1, the detector 108 is arranged on the gantry 101 opposite to the source of radiation 104, such that the surface of the detector 108 is covered by the cone beam 106. The detector 108 depicted in FIG. 1 comprises a plurality of detector elements 123 each capable of detecting X-rays which have been scattered by or passed through the object of interest 107.

During scanning the object of interest 107, the source of radiation 104, the aperture system 105 and the detector 108 are rotated along the gantry 101 in the direction indicated by an arrow 116. For rotation of the gantry 101 with the source of radiation 104, the aperture system 105 and the detector 108, the motor 103 is connected to a motor control unit 117, which is connected to a control unit 118 (which might also be denoted as a calculation or determination unit).

In FIG. 1, the object of interest 107 is a human being which is disposed on an operation table 119. During the scan of a heart 130 of the human being 107, while the gantry 101 rotates around the human being 107, the operation table 119 displaces the human being 107 along a direction parallel to the rotational axis 102 of the gantry 101. By this, the heart 130 is scanned along a helical scan path. The operation table 119 may also be stopped during the scans to thereby measure signal slices. It should be noted that in all of the described cases it is also possible to perform a circular scan, where there is no displacement in a direction parallel to the rotational axis 102, but only the rotation of the gantry 101 around the rotational axis 102.

Moreover, an electrocardiogram device 135 is provided which measures an electrocardiogram of the heart 130 of the human being 107 while X-rays attenuated by passing the heart 130 are detected by detector 108. The data related to the measured electrocardiogram are transmitted to the control unit 118.

Further, it shall be emphasized that, as an alternative to the cone-beam configuration shown in FIG. 1, the invention can be realized by a fan-beam configuration. In order to generate a primary fan-beam, the aperture system 105 can be configured as a slit collimator.

The detector 108 is connected to the control unit 118. The control unit 118 receives the detection result, i.e. the read-outs from the detector elements 123 of the detector 108 and determines a scanning result on the basis of these read-outs. Furthermore, the control unit 118 communicates with the motor control unit 117 in order to coordinate the movement of the gantry 101 with motors 103 and 120 with the operation table 11.

The control unit 118 may be adapted for reconstructing an image from read-outs of the detector 108. A reconstructed image generated by the control unit 118 may be output to a display (not shown in FIG. 1) via an interface 122.

The control unit 118 may be realized by a data processor to process read-outs from the detector elements 123 of the detector 108.

The computer tomography apparatus shown in FIG. 1 captures multi-cycle cardiac computer tomography data of the heart 130. In other words, when the gantry 101 rotates and when the operation table 119 is shifted linearly, then a helical scan is performed by the X-ray source 104 and the detector 108 with respect to the heart 130. During this helical scan, the heart 130 may beat a plurality of times. During these beats, a plurality of cardiac computer tomography data are acquired. Simultaneously, an electrocardiogram is measured by the electrocardiogram unit 135. After having acquired these data, the data are transferred to the control unit 118, and the measured data may be analyzed retrospectively.

The measured data, namely the cardiac computer tomography data and the electrocardiogram data are processed by the control unit 118 which may be further controlled via a graphical user-interface (GUI) 140. This retrospective analysis is based on a helical cardiac cone beam reconstruction scheme using retrospective ECR gating. It should be noted, however, that the present invention is not limited to this specific data acquisition and reconstruction.

However, in addition to the conventional ECR scheme, the device 118 is adapted to analyze the multi-cycle cardiac computer tomography data detected by attenuating X-rays passing the heart 113 in the following manner, to eliminate artifacts: A determination unit 118 locates a high contrast object within the first volume and locates the high contrast object within the second volume. Then, a determination of a motion vector field for the high contrast object is performed, resulting in a first motion vector for the first volume and a second motion vector for the second volume. Then, the device 118 performs a motion compensated reconstruction on the basis of the motion vector field.

Figure 2:
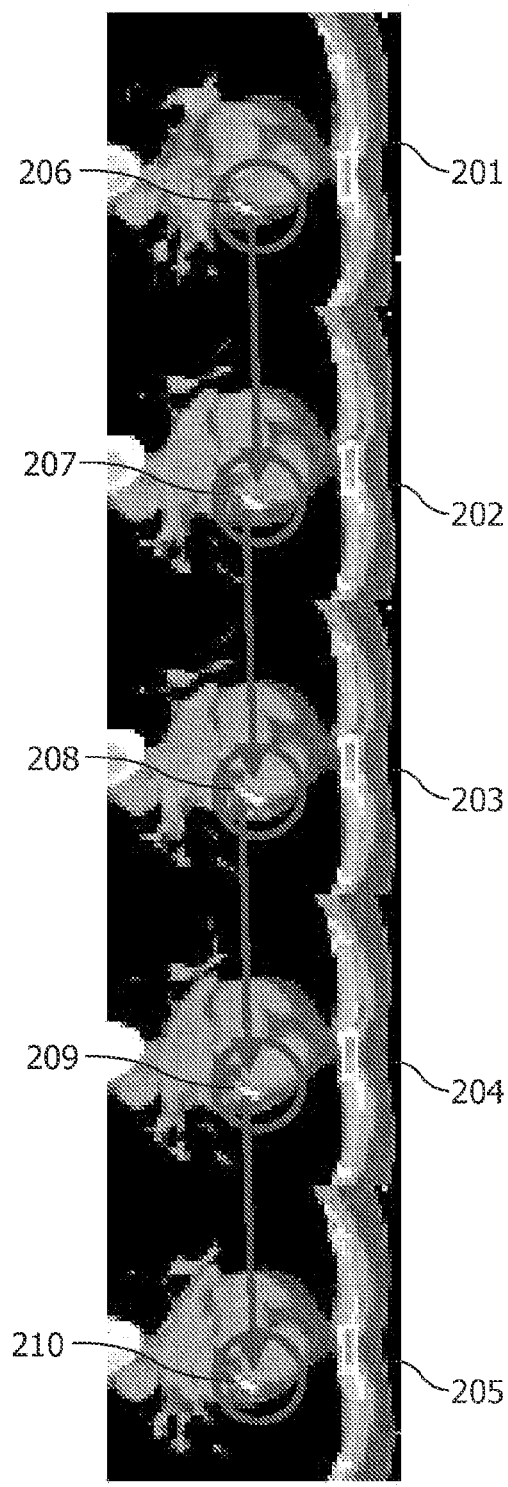
FIG. 2 shows a schematic representation of a calcium scoring data set reconstructed at different phase points.

FIG. 2 shows a schematic representation of a calcium scoring data set at different phase points. The data set depicted in FIG. 2 is reconstructed at every 20% cardiac cycle showing a high contrast calcification 206, 207, 208, 209, 210 in a coronary artery which can be followed through the phases 201, 202, 203, 204, 205.

It should be noted that the images 201-205 at different phases are shown at different slices to track the calcification in three dimensions.

Figure 3:
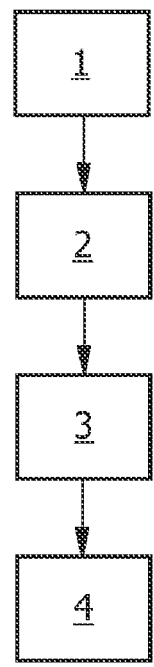
FIG. 3 shows a flow-chart of an exemplary method according to the present invention.

FIG. 3 shows a flow-chart of an exemplary method according to the present invention for performing a motion compensated CT reconstruction of high contrast objects. It should be noted, however, that the method may be applied not only to data sets acquired with a CT examination apparatus, but may also be applied to other data sets, which are acquired by other examination apparatuses, such as, for example, positron emission computed tomography systems.

The method starts at step 1 with the emission of electromagnetic radiation by a radiation source to the object of interest. Furthermore, a conventional CT scan is performed, resulting in an acquisition of projection data. Furthermore, also in step 1, an acquisition of electrocardiogram data is performed.

Then, in step 2, the projection data, for example acquired in a low pitch helical acquisition mode or during a circular scan, or during any other scan, such as, for example, a saddle trajectory scan, together with the ECG data are reconstructed at different phase points. Within each of the reconstructed volumes the high contrast objects are located with a suitable segmentation algorithm. For example, the segmentation algorithm may be a simple threshholding approach, which sets all Housfield values below a certain value (threshhold) to zero and thus delivers an image, which contains only the high contrast structures—if the threshhold has been chosen appropriately. A different segmentation method may contain information about the shape of the object to be segmented, calculation the local grey value distribution and there first and second derivative. Finally, model based segmentation may be of high interest in view of the motion compensated reconstruction of stents, since the shape and material of a deployed stent in a vessel is approximately known.

If there is more than one high contrast object, the correspondence of the object in the different data sets may be determined, for example via the most similar shape.

Then, in step 3, the motion vector field for each of the target objects is determined from the different volume data set by calculating for example the displacement vectors of the corresponding objects from phase to phase. As a result, the three-dimensional motion vectors are obtained for all the phases which have been reconstructed.

Finally, in step 4, a motion compensated reconstruction is carried out, where those projections are used for the reconstruction, which cover the cardiac phases for which the motion compensation has to be performed. In other words, since the gated reconstruction in CT imaging may always require a finite sized temporal window from which the data are taken for the reconstruction process, the motion compensation should be performed for all projections within this window. Since the image volumes may always be built up from the complete temporal measurement interval and seen as the mean of this interval, the same happens for an image reconstructed at the end or the beginning of the interval chosen for the central image to be motion compensated. Though they may employ the same projection data for the generation of volume data, they are treated as different temporal states—which is—to a large extend—true. At this point it is referred to the above explanations with respect to the temporal interpolation.

These can be all projections, provided the motion estimation covers the complete cardiac cycle, or they may be only one part of the complete projections. The motion compensated reconstruction may cover a sub-volume containing the structure of interest and the motion vectors may be used directly in the reconstruction process by modifying the voxel positions in the volume according to cardiac phase of the projection to be back-projected.

Alternatively, the complete volume may be reconstructed motion compensated after a spatial extra-/interpolation of the motion vectors at the different volume positions. A possible interpolation method may be the thin plate spline interpolation or a simple tri-linear interpolation.

A full three-dimensional motion compensated reconstruction may be achieved with the described method for a target volume of interest or for the complete volume. It may be used to increase the temporal resolution of the data set or to decrease motion blurring. In addition, it may help to use wider gating windows in cardiac CT imaging which may lead to an increased signal-to-noise ratio.

Figure 4:
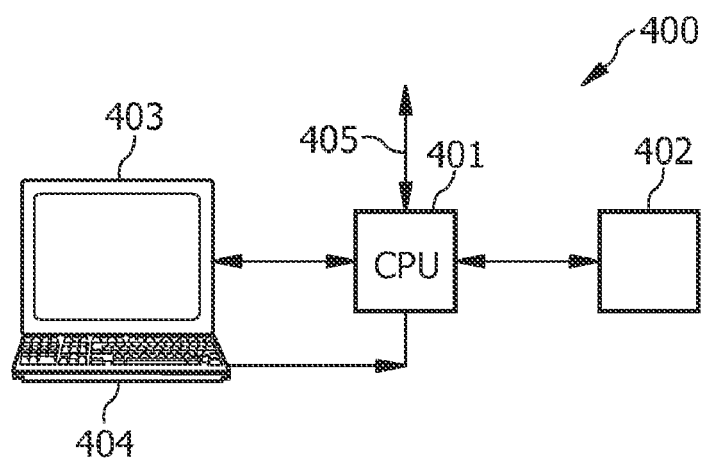
FIG. 4 shows an exemplary embodiment of an image processing device according to the present invention, for executing an exemplary embodiment of a method in accordance with the present invention.

FIG. 4 depicts an exemplary embodiment of a data processing device 400 according to the present invention for executing an exemplary embodiment of a method in accordance with the present invention. The data processing device 400 depicted in FIG. 4 comprises a central processing unit (CPU) or image processor 401 connected to a memory 402 for storing an image depicting an object of interest, such as a patient or an item of baggage. The data processor 401 may be connected to a plurality of input/output network or diagnosis devices, such as a CT device. The data processor 401 may furthermore be connected to a display device 403, for example, a computer monitor, for displaying information or an image computed or adapted in the data processor 401. An operator or user may interact with the data processor 401 via a keyboard 404 and/or other output devices, which are not depicted in FIG. 4.

Furthermore, via the bus system 405, it may also be possible to connect the image processing and control processor 401 to, for example, a motion monitor, which monitors a motion of the object of interest. In case, for example, a lung of a patient is imaged, the motion sensor may be an exhalation sensor. In case the heart is imaged, the motion sensor may be an electrocardiogram.

Exemplary embodiments of the invention may be sold as a software option to CT scanner console, imaging workstations or PACS workstations.

According to an aspect of the present invention, high quality cardiac reconstruction of target structures with a high contrast like calcified plaque or devices like stents may be performed with improved temporal resolution, decreased motion blurring or improved signal-to-noise ratio or decreased dose.

It should be noted that the term "comprising" does not exclude other elements or steps and the "a" or "an" does not exclude a plurality. Also elements described in association with different embodiments may be combined.

It should also be noted that reference signs in the claims shall not be construed as limiting the scope of the claims.

The invention claimed is:

1. An examination apparatus for examination of an object of interest, the examination apparatus comprising:
   a reconstruction unit adapted for reconstructing, on the basis of a data set, a first volume of the object of interest corresponding to a first phase point and a second volume of the object of interest corresponding to a second phase point;
   a determination unit adapted for:
   locating a high contrast object within the first volume and locating the high contrast object within the second volume; and
   determining a motion vector field for the high contrast object, resulting in a motion vector connecting the positions of the high contrast object in the first volume and the second volume;
   wherein the reconstruction unit is further adapted for performing a motion compensated reconstruction on the basis of the motion vector field.

2. The examination apparatus of claim 1,
   wherein the data set comprises projection data comprising projections of the object of interest and electrocardiogram data of the object of interest.

3. The examination apparatus of claim 2,
   wherein the projection data comprises first projections;
   wherein the motion compensated reconstruction is performed for the first projections of the projection data, the first projections covering phases for which a motion compensation has been performed.

4. The examination apparatus of claim 3,
   wherein the first projections, which cover phases for which a motion estimation and the motion compensation have been performed, are all projections of the data set; and
   wherein the motion estimation covers a complete cardiac cycle.

5. The examination apparatus of claim 3,
   wherein the first projections, which cover phases for which the motion estimation and the motion compensation have been performed, are a selection of the projections of the data set; and
   wherein the motion estimation covers only parts of the cardiac cycle.

6. The examination apparatus of claim 1,
wherein the motion compensated reconstruction covers a sub-volume of at least one of the first volume and the second volume;
wherein the sub-volume comprises the high contrast object;
wherein the motion vectors are used directly in the motion compensated reconstruction by modifying a voxel position in the sub-volume according to a cardiac phase of the projection to be back-projected.

7. The examination apparatus of claim 1,
wherein the motion compensated reconstruction covers at least one of the complete first volume and the complete second volume;
wherein the motion compensated reconstruction is performed after at least one of a spatial extrapolation and a spatial interpolation of the first and second motion vectors.

8. The examination apparatus of claim 7,
wherein the interpolation is a thin plate spline interpolation.

9. The examination apparatus of claim 1,
wherein the motion compensated reconstruction is performed after a temporal interpolation of the motion vectors.

10. The examination apparatus of claim 1, further comprising:
a radiation source adapted for moving along a scan path and for emitting electromagnetic radiation to the object of interest;
a detector unit adapted for detecting the projection data; and
an electrocardiogram unit adapted for detecting the electrocardiogram data;
wherein the examination apparatus is adapted for acquiring the projection data in a low pitch helical acquisition mode; and
wherein the reconstruction is a gated reconstruction.

11. The examination apparatus of claim 1,
wherein locating the high contrast object within the first volume and within the second volume comprises:
a location of a first high contrast object within the first volume;
a location of a second high contrast object within the second volume; and
a determination of a correspondence of the first high contrast object and the second high contrast object.

12. The examination apparatus of claim 1, configured as one of the group consisting of a material testing apparatus, a medical application apparatus and a micro CT system.

13. The examination apparatus of claim 1, configured as one of the group consisting of a computer tomography apparatus, a coherent scatter computed tomography apparatus, a positron emission computed tomography apparatus, a single photon emission computed tomography apparatus, and an interventional 3D rotational X-ray device.

14. The examination apparatus of claim 1,
further comprising a collimator arranged between the electromagnetic radiation source and the detector unit;
wherein the collimator is adapted for collimating an electromagnetic radiation beam emitted by the electromagnetic radiation source to form a cone-beam or a fan-beam.

15. An image processing device for examination of an object of interest, the image processing device comprising:
a memory for storing a data set data of the object of interest;
a reconstruction unit adapted for reconstructing, on the basis of the data set, a first volume of the object of interest corresponding to a first phase point and a second volume of the object of interest corresponding to a second phase point;
a determination unit adapted for:
locating a high contrast object within the first volume and locating the high contrast object within the second volume; and
determining a motion vector field for the high contrast object wherein the motion vector field connects the position of the high contrast object in the first volume and the second volume;
wherein the reconstruction unit is further adapted for performing a motion compensated reconstruction on the basis of the motion vector field.

16. A method of examination of an object of interest, method comprising the steps of:
reconstructing, on the basis of a data set, a first volume of the object of interest corresponding to a first phase point and a second volume of the object of interest corresponding to a second phase point;
locating a high contrast object within the first volume and locating the high contrast object within the second volume; and
determining a motion vector field for the high contrast object, resulting in a motion vector connecting the position of the high contrast object in the first volume and the second volume;
wherein the reconstruction unit is further adapted for performing a motion compensated reconstruction on the basis of the motion vector field.

17. A computer-readable medium, in which a computer program of examination of an object of interest is stored which, when being executed by a processor, is adapted to carry out the steps of:
reconstructing, on the basis of a data set, a first volume of the object of interest corresponding to a first phase point and a second volume of the object of interest corresponding to a second phase point;
locating a high contrast object within the first volume and locating the high contrast object within the second volume; and
determining a motion vector field for the high contrast object, resulting in a motion vector connecting the positions of the high contrast object in the first volume and the second volume;
wherein the reconstruction unit is further adapted for performing a motion compensated reconstruction on the basis of the motion vector field.

18. A program element of examination of an object of interest, which, when being executed by a processor, is adapted to carry out the steps of:
reconstructing, on the basis of a data set, a first volume of the object of interest corresponding to a first phase point and a second volume of the object of interest corresponding to a second phase point;
locating a high contrast object within the first volume and locating the high contrast object within the second volume; and
determining a motion vector field for the high contrast object, resulting in a motion vector connecting the positions of the high contrast object in the first volume and the second volume;
wherein the reconstruction unit is further adapted for performing a motion compensated reconstruction on the basis of the motion vector field.

* * * * *